United States Patent
Higaki et al.

(10) Patent No.: US 9,625,539 B2
(45) Date of Patent: Apr. 18, 2017

(54) MAGNET EVALUATING DEVICE AND METHOD

(71) Applicant: Nissan Motor Co., Ltd., Yokohama-shi, Kanagawa (JP)

(72) Inventors: Koji Higaki, Yokohama (JP); Kimio Nishimura, Yokohama (JP); Masahiro Omata, Yokohama (JP); Hideki Watanabe, Sagamihara (JP); Yasuhisa Koike, Fujisawa (JP); Takashi Sekikawa, Yokohama (JP); Yasushi Matsushita, Yokohama (JP); Akihisa Hori, Yokohama (JP); Takumi Ohshima, Yokohama (JP); Michito Kishi, Atsugi (JP); Kiyoshi Hasegawa, Yokohama (JP); Hiroaki Shibukawa, Machida (JP); Kazuhiro Takaichi, Yokohama (JP); Hideo Sakuyama, Tokyo (JP); Yuhei Yamane, Yokohama (JP); Yoshito Ozawa, Wako (JP)

(73) Assignee: Nissan Motor Co., Ltd., Yokohama (JP)

( * ) Notice: Subject to any disclaimer, the term of this patent is extended or adjusted under 35 U.S.C. 154(b) by 139 days.

(21) Appl. No.: 14/764,085

(22) PCT Filed: Feb. 10, 2014

(86) PCT No.: PCT/JP2014/053083
§ 371 (c)(1),
(2) Date: Jul. 28, 2015

(87) PCT Pub. No.: WO2014/129348
PCT Pub. Date: Aug. 28, 2014

(65) Prior Publication Data
US 2016/0011282 A1  Jan. 14, 2016

(30) Foreign Application Priority Data

Feb. 25, 2013  (JP) ................. 2013-034501

(51) Int. Cl.
*G01N 27/74*  (2006.01)
*G01R 33/12*  (2006.01)
(Continued)

(52) U.S. Cl.
CPC .......... *G01R 33/12* (2013.01); *G01N 27/9026* (2013.01); *G01R 33/10* (2013.01); *H01F 41/0253* (2013.01)

(58) Field of Classification Search
CPC .... G01R 33/0035; G01R 33/10; G01R 33/12; G01R 33/123; G01R 33/14; G01N 27/72;
(Continued)

(56) References Cited

U.S. PATENT DOCUMENTS 6,337,450 B1 * 1/2002 Tanii ...................... B07C 5/344
209/575
2008/0238417 A1 * 10/2008 Suzuki .................. G01R 33/12
324/228

(Continued)

FOREIGN PATENT DOCUMENTS

EP  1009049 A2  6/2000
JP  53-20986 A  2/1978
(Continued)

*Primary Examiner* — Arleen M Vazquez
*Assistant Examiner* — Steven Yeninas
(74) *Attorney, Agent, or Firm* — Global IP Counselors, LLP (57) ABSTRACT

A magnet evaluating device evaluates an evaluation magnet by passing the evaluation magnet, which is formed by connecting a plurality of magnetic sections with insulating material in between, and a master magnet of the same form through an alternating magnetic field generated by an excitation coil, measuring the eddy current occurring in the magnetic section as voltage or current occurring in a detection coil and comparing the measured value for the evaluation magnet and the measured value for the master magnet.

9 Claims, 7 Drawing Sheets (51) Int. Cl.
*G01R 33/10* (2006.01)
*G01N 27/90* (2006.01)
*H01F 41/02* (2006.01)

(58) Field of Classification Search
CPC ...... G01N 27/82; G01N 27/90; G01N 27/902; G01N 27/9013; G01N 27/9026; G01N 27/9033; G01N 27/9086
USPC ....... 324/205, 206, 222, 225, 228, 234, 238, 324/239, 240, 261, 262
See application file for complete search history.

(56) References Cited

U.S. PATENT DOCUMENTS

| | | | | |
|---|---|---|---|---|
| 2009/0167298 | A1* | 7/2009 | Kreutzbruck | G01N 27/9033 324/235 |
| 2013/0076348 | A1* | 3/2013 | Ide | G01N 27/90 324/232 |

FOREIGN PATENT DOCUMENTS

| | | |
|---|---|---|
| JP | 2001-174438 A | 6/2001 |
| JP | 2003-234225 A | 8/2003 |
| JP | 2008-58054 A | 3/2008 |
| JP | 2009-33958 A | 2/2009 |
| JP | 2009-142081 A | 6/2009 |

\* cited by examiner

MAGNET EVALUATING DEVICE AND METHOD

CROSS-REFERENCE TO RELATED APPLICATIONS

This application is a U.S. National stage application of International Application No. PCT/JP2014/053083, filed Feb. 10, 2014, which claims priority to Japanese No. 2013-034501 filed in Japan on Feb. 25, 2013, the contents of each of which is hereby incorporated herein by reference.

BACKGROUND

Field of the Invention

The present invention relates to a magnet evaluating device for evaluating a permanent magnet and a method thereof and, specifically, to a magnet evaluating device for evaluating the quality of a permanent magnet by detecting an eddy current occurring in a magnet and a method thereof.

Background Information

In a conventional device for evaluating an eddy current loss of a magnet, an evaluation magnet is put in an insulated sample chamber, the evaluation magnet is subjected to a magnetic field, and the temperature is measured by attaching a thermocouple to the evaluation magnet (for example, Japanese Laid-Open Patent Application No. 2003-234225). This conventional device evaluates a magnet by capturing the eddy current loss as the heat generated by the loss.

SUMMARY

In the prior art, providing a sample chamber that is sufficiently insulated to cut off changes in the ambient temperature is necessary in order to capture the eddy current loss as the heat generated thereby. Also, a large magnetic field generation device is necessary in order for the magnetic field to reach the magnet placed in the sample chamber, through the sample chamber.

Consequently, an increase in the total size cannot be avoided with a conventional device, which is one cause of the high costs of the device.

Thus, an object of the present invention is to provide a magnet evaluating device with a simpler configuration that is capable of evaluating the eddy current loss occurring in a magnet, as well as a magnet evaluating method using this device.

To achieve the above objective, the magnet evaluating device according to the present invention comprises an excitation coil that generates a magnetic field of a magnitude within a range corresponding to a region including an insulating material between at least one magnetic section of a magnet, which is formed by connecting a plurality of magnetic sections with insulating material in between, and another magnetic section that is adjacent to the one magnetic section; a detection coil for detecting an eddy current occurring in the magnet; a holder to which are set an evaluation magnet, which is formed by connecting a plurality of magnetic sections with insulating material in between, and a master magnet, which is formed by connecting a plurality of magnetic sections with insulating material in between; a transfer unit that transfers the holder into which are set the evaluation magnet and the master magnet through the magnetic field; and an evaluation unit for comparing a measured value, measuring a voltage or a current generated in the detection coil when the evaluation magnet passes through the magnetic field, and a measured value, measuring the voltage or the current generated in the detection coil when the master magnet passes through the magnetic field.

Additionally, to achieve the above objective, the magnet evaluating method according to the present invention uses a magnet evaluating device comprising: an excitation coil that generates a magnetic field of a magnitude within a range corresponding to a region including an insulating material between at least one magnetic section of a magnet, which is formed by connecting a plurality of magnetic sections with insulating material in between, and another magnetic section that is adjacent to the one magnetic section; a detection coil for detecting an eddy current occurring in the magnet; and a holder into which are set an evaluation magnet, which is formed by connecting a plurality of magnetic sections with insulating material in between, and a master magnet, which is formed by connecting a plurality of magnetic sections with insulating material in between; and a transfer unit that transfers the holder into which are set the evaluation magnet and the master magnet through the magnetic field; to evaluate an evaluation magnet by causing the transfer unit to pass the evaluation magnet and the master magnet through the magnetic field and comparing a voltage or a current generated in the detection coil when the evaluation magnet passes through the magnetic field, and the voltage or the current generated in the detection coil when the master magnet passes through the magnetic field that is transferred by the transfer unit.

The present invention comprises an excitation coil for providing a magnetic field to an evaluation magnet and a detection coil for detecting an eddy current that is occurring in the evaluation magnet. The excitation coil generates a magnetic field of a magnitude within a range corresponding to a region including an insulating material between at least one magnetic section of an evaluation magnet, which is formed by connecting a plurality of magnetic sections with insulating material in between, and another magnetic section that is adjacent to the one magnetic section. Then, the evaluation magnet is transferred, along with a master magnet, which is known beforehand to have an eddy current loss that is equal to or less than a predetermined value, to the excitation coil and the detection coil. The present invention is configured to then evaluate the evaluation magnet by measuring and comparing the voltage or the current generated in the detection coil when transferring the evaluation magnet and the master magnet. Accordingly, the eddy current occurring in a magnet can be directly measured and evaluated; as a result, a large sample chamber as in the prior art becomes unnecessary, and reducing the size of the device configuration becomes possible.

BRIEF DESCRIPTION OF THE DRAWINGS

Referring now to the attached drawings which form a part of this original disclosure.

FIGS. 1A-1C are views showing the configuration of the magnet evaluating device according to the present invention.

DETAILED DESCRIPTION OF THE EMBODIMENTS

Embodiments of the present invention will be explained below, with reference to the appended drawings. In the explanations of the drawings, the same elements have been given the same reference codes, and the overlapping explanations have been omitted. The sizes and ratios of the members in the drawing have been exaggerated for the convenience of the explanation, and they are different from the actual sizes and ratios.

Figure 1A:
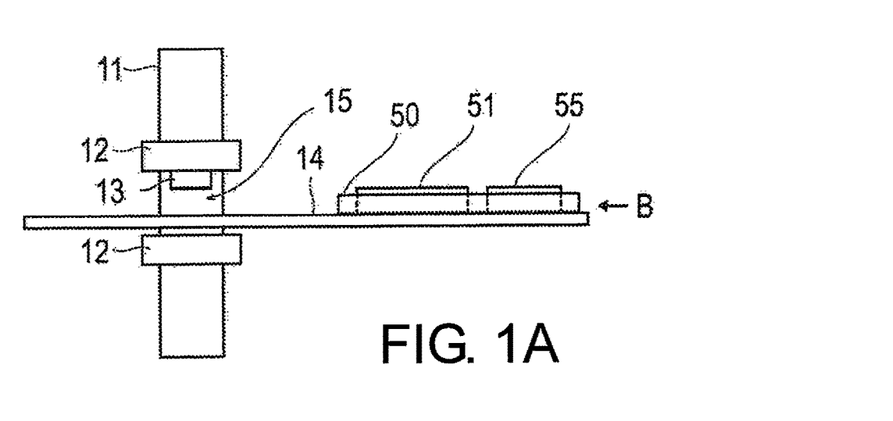
FIG. 1A is a front view.
Figure 1B:
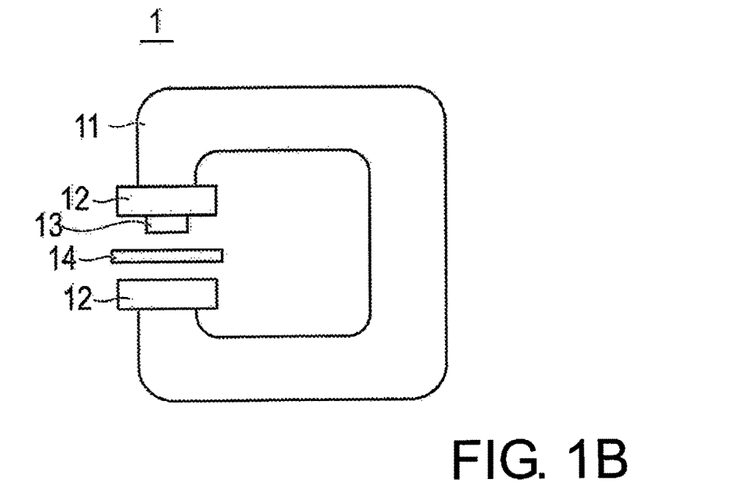
FIG. 1B is a side view seen from the arrow B direction in FIG. 1A.
Figure 1C:
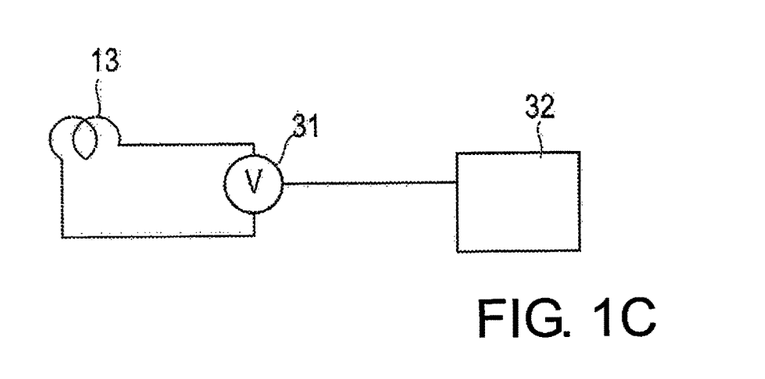
FIG. 1C is a block view of the detection coil system.

FIGS. 1A-1C are views showing the configuration of the magnet evaluating device according to the present invention; FIG. 1A is a front view, FIG. 1B is a side view seen from the arrow B direction in FIG. 1A (excluding a holder 50 in FIG. 1A), and FIG. 1C is a block view of the detection coil system.

This magnet evaluating device 1 comprises a C-shaped yoke 11, an excitation coil 12, and a detection coil 13. The device also comprises a conveyor 14 for transferring an evaluation magnet 51 and a master magnet 55 so as to continuously pass them through the divided portion (evaluation position 15) of the C-shaped yoke 11. This conveyor 14 (transfer unit) transfers the evaluation magnet 51 and the master magnet 55 after setting the two in a holder 50 for aligning and continuously feeding the evaluation magnet and the master magnet (this is described in detail below).

A voltmeter 31 (refer to FIG. 1C) is connected to the two ends of the coil wire of the detection coil 13. The measured value of the voltmeter 31 is input into a computer 32 (refer to FIG. 1C) to determine the quality of the magnet. The computer 32 is an evaluation unit.

The yoke 11 is for forming a magnetic path. The yoke 11, which may be any type that is iron-core, is generally used as a material for forming a magnetic path, such as those in which ferrite plates are laminated.

The excitation coil 12 is wound around the yoke 11. By supplying a high-frequency current (an alternating current) to this excitation coil 12, an alternating magnetic field is also generated in the divided portion (evaluation position 15) of the C-shape via the yoke 11. The excitation coil 12 is wound so as not to protrude from the vicinity of the divided portion of the C-shape of the yoke 11 (the divided portion of the yoke 11) in order to generate a powerful magnetic field in the evaluation position 15 as efficiently as possible.

The magnetic flux of the alternating magnetic field generated by the excitation coil 12 passes through the evaluation magnet 51 and the master magnet 55 by passing the evaluation magnet 51 and the master magnet 55 through this C-shaped divided portion. At this time, an eddy current in a direction that cancels the alternating magnetic field is generated in the evaluation magnet 51 and the master magnet 55.

The high-frequency current that is applied to the excitation coil 12 may be appropriately set in accordance with the purpose of the magnet to be evaluated. For example, when evaluating a magnet used for a driving motor of an electric vehicle or a hybrid vehicle, evaluating the eddy current loss in a state close to a state of being actually mounted on a motor becomes possible by applying a high-frequency current with a frequency corresponding to the maximum rotational speed of the motor and a frequency corresponding to a higher harmonic thereof.

On the other hand, the voltage of the high-frequency current to be applied to the excitation coil 12, that is, the strength of the alternating magnetic field to be generated, may be any value that is capable of detecting an eddy current in the detection coil 13 (described in detail below).

The high-frequency current is continuously applied to the excitation coil 12 while the evaluation magnet 51 and the master magnet 55 are passing through the evaluation position 15.

The detection coil 13 comprises at least one coil for detecting an eddy current occurring in the evaluation magnet 51 and the master magnet 55. When an eddy current occurs in the evaluation magnet 51 and the master magnet 55, a dielectric current is generated in the detection coil 13 by the eddy current. The voltage generated in the detection coil 13 can be measured by attaching a voltmeter 31 to the two coil ends of this detection coil 13, the value of which becomes the eddy current amount. The loss caused by the eddy current loss (eddy current loss) gives rise to an exothermic phenomenon.

Other than a voltmeter, the current generated in the detection coil 13 may be detected as a current value flowing in the detection coil by attaching, for example, an ammeter. Also, the voltage fluctuation waveform may be directly observed by connecting a synchroscope to the detection coil 13.

This detection coil 13 is disposed coaxially with the excitation coil 12 while maintaining a clearance that will not interfere with the continuous movement of the evaluation magnet 51 and the master magnet 55.

The conveyor 14 is, for example, a belt conveyor that continuously transfers, at a set speed, the holder 50, to which the evaluation magnet 51 and the master magnet 55 are set, so that the holder passes the evaluation position 15. The conveyor 14, at least the portion of which that enters the magnetic field, is formed from a non-magnetic, non-conductive body, so that an induction current is not generated in the magnetic field. This is because, if a magnetic body or a conductive body enters the magnetic field, the magnetic field is disturbed, and measurement errors occur due to an eddy current thereby generated. Accordingly, for example, rubber and resin material are preferable as the material for the conveyor.

The holder 50 aligns and holds the evaluation magnet 51 and the master magnet 55. By using this holder 50, the relative positional relationship of the evaluation magnet 51 and the master magnet 55 is always aligned; thus, taking the evaluation magnet 51 and the master magnet 55 to the same position within the evaluation position 15 becomes easier, as compared to when individually placing the evaluation magnet 51 and the master magnet 55 on the conveyor 14. The holder 50 is made using a non-magnetic, non-conductive material, such as rubber, resin, or ceramic, so that an induction current is not generated in the magnetic field.

The holder 50 may be omitted, and the evaluation magnet 51 and the master magnet 55 may be kept aligned directly on the conveyor. The evaluation magnet 51 and the master magnet 55 set in the holder may be passed through the evaluation position 15 by a robot arm, etc., instead of a conveyor.

The computer 32 (evaluation unit) detects the voltage from the current generated in the detection coil 13 to determine the quality of the evaluation magnet 51. While the details of this determination method are described below, in short, a current value detected in the master magnet 55 is set as a threshold value; if the current from the evaluation magnet 51 is equal to or less than this threshold value, the evaluation magnet is determined to be good.

The computer 32 comprises a display to show the determination results, similar to a common computer. The computer may also comprise a communication means and be connected to a host computer for process management or to a server, etc. for storing the determination results.

The evaluation magnet 51, which is the evaluation magnet in the present embodiment, will be described next.

Figure 2A:
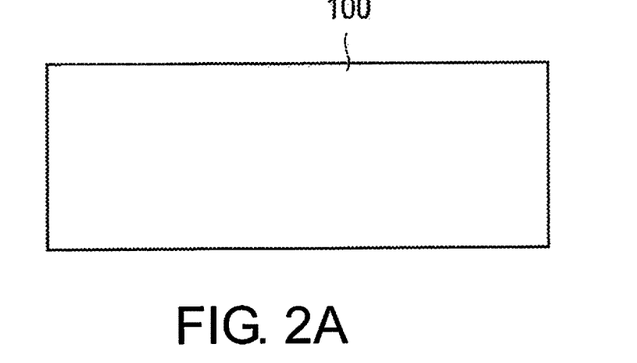
FIGS. 2A-2C are schematic views showing the evaluation magnet.
Figure 2B:
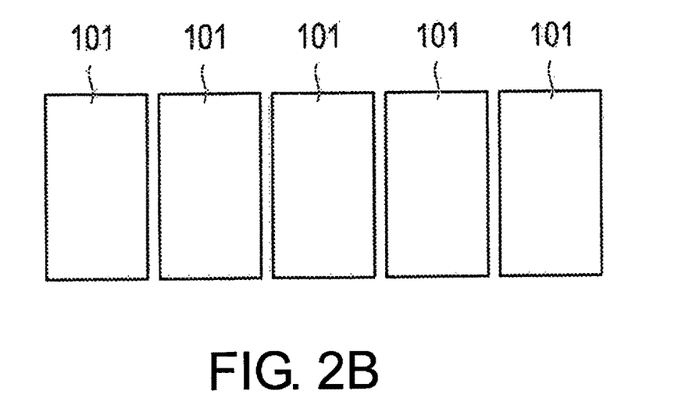
Figure 2C:
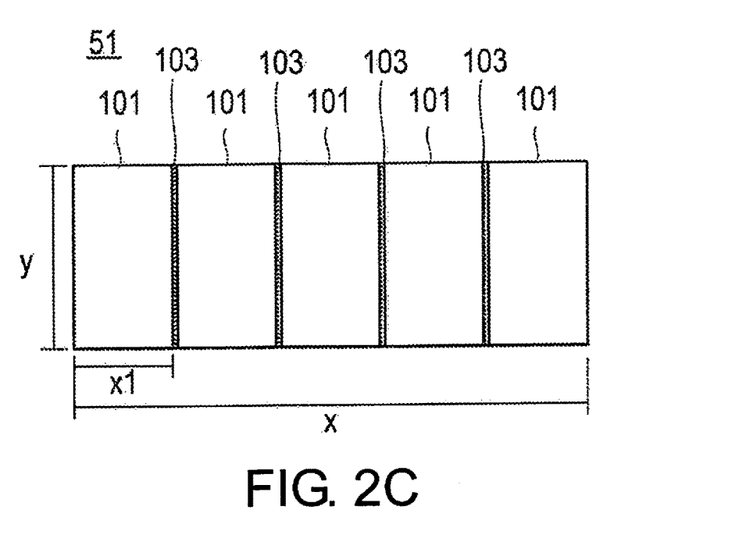

FIGS. 2A-2C are schematic views showing the evaluation magnet.

As illustrated in FIG. 2A, the evaluation magnet 51 is a magnet made by cleaving what was originally one integrated permanent magnet 100 into a plurality of magnetic sections 101, as illustrated in FIG. 2B, which are then reconnected at the cleavage plane, as illustrated in FIG. 2C. This type of magnet is referred to as a cleaved and reconnected magnet. The connection is achieved via bonding and integrating by applying an adhesive to the cleavage plane. There are other configurations, such as integrating with a resin molding after forming an insulating film by oxidizing the cleavage plane or sandwiching an insulating material. Therefore, both in the case of bonding and in the case of resin molding, the evaluation magnet 51 is configured so that magnetic sections are connected at the cleavage plane with insulating material 103 in between. Of course, the connected magnet (evaluation magnet 51) is also a permanent magnet. In FIG. 2C, x indicates the longitudinal full length of the evaluation magnet 51, and x1 indicates the length of one magnetic section 101 (here, the plurality of magnetic sections 101 are described as each having the same length x1, but the lengths may be different). The y indicates the width of the evaluation magnet 51.

Such a magnet made by reconnecting after cleaving one permanent magnet 100 is disclosed in, for example, Japanese Laid-Open Patent Application No. 2009-33958 and Japanese Laid-Open Patent Application No. 2009-142081. In the present embodiment, in addition to magnets made by reconnecting after cleaving what was originally one magnet, as those disclosed in these publications, permanent magnets made by integrating magnetic sections, which were formed separately, with insulating material in between can also be evaluated.

The master magnet 55, while not shown, is a magnet made by connecting and integrating a plurality of magnetic sections, which are permanent magnets, with insulating material in between, in the same way as the evaluation magnet 51. In order to use this as a master magnet 55, a magnet that is known to have an eddy current loss of equal to or less than a predetermined value is used.

The master magnet 55 preferably has the same form as the evaluation magnet 51. That is, if the evaluation magnet 51 is a magnet made by reconnecting after cleaving one permanent magnet, a magnet made by reconnecting after cleaving one permanent magnet should also be used as the master magnet 55. If the evaluation magnet 51 is a magnet made by connecting a plurality of permanent magnets, which were individually made, a magnet made by connecting a plurality of permanent magnets, which were individually made, should also be used as the master magnet 55. In addition, the size of the master magnet (total length x, width y, and the length x1 of individual magnets) is preferably the same as the evaluation magnet 51.

However, even when of the same form, the number of connected magnetic sections may be different. For example, if the evaluation magnet 51 consists of three or more (for example, three, four, five, . . . ten, or even more) magnetic sections, the master magnet 33 can sufficiently have at least three magnetic sections. The reasons for this are as follows. During an evaluation of the evaluation magnet 51, the voltage detected by the detection coil is different for a magnetic section on the end and for a magnetic section sandwiched between magnetic sections on both adjacent sides (described in detail below). Accordingly, the master magnet 55 should have a magnetic section that is on the end and a magnetic section that has magnetic sections on both adjacent sides; therefore, so a master magnet 55 is configured from at least three magnetic sections. Meanwhile, if there is a plurality of magnetic sections between magnetic sections on both adjacent sides, as long as each one is a normal magnetic section, the voltage that is generated in the detection coil will not show a significantly large difference. Accordingly, if the master magnet 55 is configured from at least three magnetic sections, evaluating an evaluation magnet 51 consisting of three or more magnetic sections is possible. The evaluation method will be described in detail below.

In light of the form of the evaluation magnet 51 and the master magnet 55 described above, the relationship between the excitation coil 12 and the detection coil 13 in the magnet evaluating device 1 of the present embodiment will be described.

Figure 3:
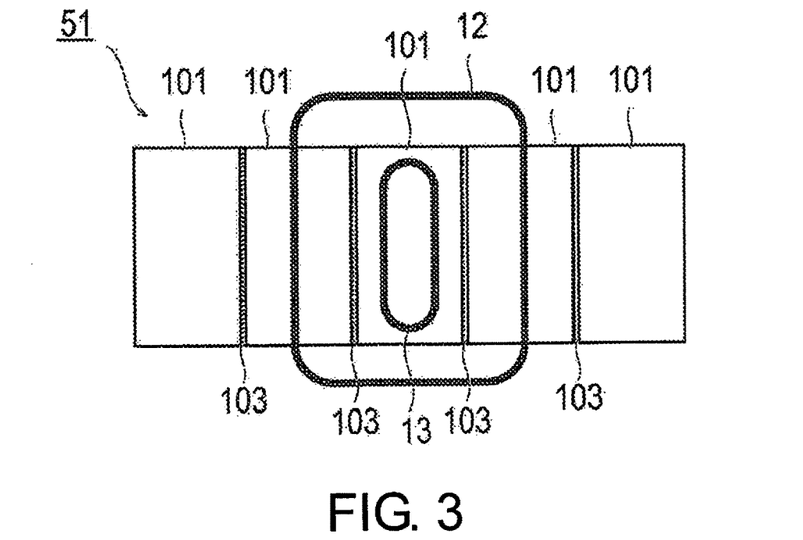
FIG. 3 is a plan view showing the relationship between the excitation coil and the detection coil.
Figure 4:
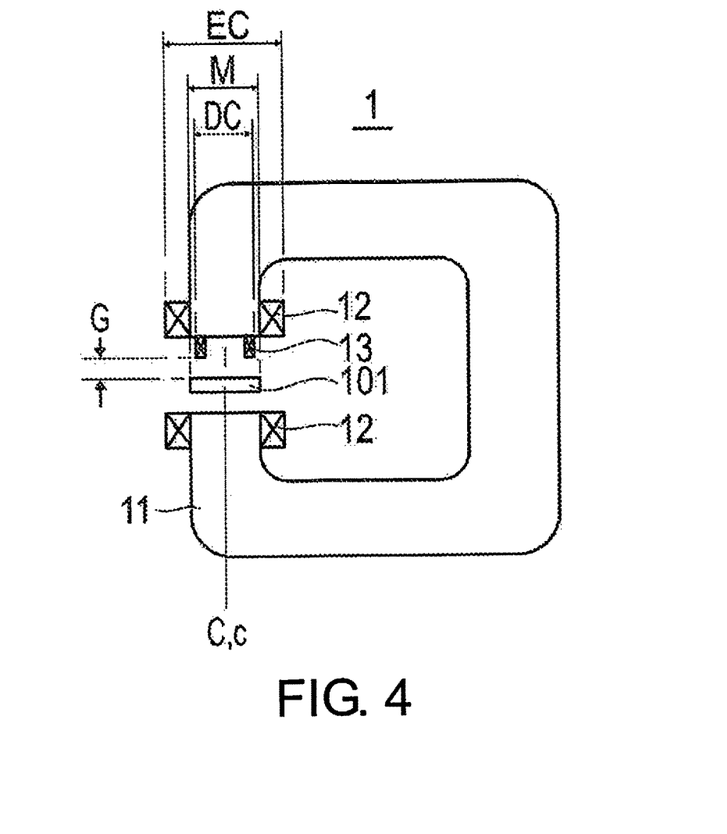
FIG. 4 is a schematic cross-sectional view at the evaluation position showing the relationship between the excitation coil, the detection coil, and the evaluation magnet (master magnet).

FIG. 3 is a plan view showing the relationship between the excitation coil, the detection coil, and the evaluation magnet (master magnet). FIG. 4 is a schematic cross-sectional view at the evaluation position (excluding the conveyor 14) showing the relationship between the excitation coil, the detection coil, and the evaluation magnet (master magnet). In FIG. 4, EC is the dimension of the excitation coil 12, DC is the dimension of the detection coil 13, and M is the dimension of the magnet; all of the directions indicated in FIG. 4 are the widths thereof (M is the same as y in FIG. 2). Also, in FIG. 4, G is the distance (gap) between the detection coil 13 and the magnetic section 101.

Here, the evaluation magnet 51 illustrated in FIG. 2 will be described as an example, but the master magnet 55 is configured in the same way.

The evaluation magnet 51 is in the form of a plurality of magnetic sections 101 that they are connected and integrated, as described above. In the present embodiment, an eddy current is detected in both the evaluation magnet 51 and the master magnet 55 for each one of the integrated, plural magnetic sections 101.

The alternating magnetic field that is applied by the excitation coil 12 tends to be generated so as to spread at the coil ends; therefore, when that the dimensions of the excitation coil and the magnet are about the same, variations occur in the magnetic field and act on the magnet ends; as a result, unevenness occurs in the eddy current generated in the magnet, affecting the accuracy of the evaluation. Therefore, by making the excitation coil 12 sufficiently large with respect to the vertical and horizontal dimensions of the magnetic section 101, a uniform alternating magnetic field can be applied to the magnetic section 101; as a result, the eddy current loss of the magnet can be evaluated with a higher accuracy. Accordingly, the longitudinal size of the excitation coil 12 should be a size that is capable of generating an alternating magnetic field of a magnitude within a range corresponding to a region including an insulating material 103 between at least one magnetic section 101 and another magnetic section 101 that is adjacent to the one magnetic section 101, as illustrated in FIG. 3. On the other hand, the widthwise size should be larger than the width of the magnetic section 101, as illustrated in FIG. 4. Therefore, the dimension EC of the excitation coil 12 should be >the dimension M of the magnet.

By configuring the size of the excitation coil 12 in this way, the alternating magnetic field that is generated by the excitation coil 12 will cover the magnetic section 101 to be evaluated and part of the region of a magnetic section 101 that is adjacent thereto.

Accordingly, the cross section of the yoke 11 (the end surface of the divided portion of the C-shape) should be larger than a range including two adjacent magnetic sections 101.

At least one magnetic section 101 to be evaluated and part of a magnetic section 101 adjacent thereto will thereby be in the alternating magnetic field; as a result, an eddy current can be generated in the magnetic section 101 that is the evaluation object, as well as in a part of an adjacent magnetic section 101 that is adjacent thereto, and this affects the magnetic section 101 that is the evaluation object.

While there is no particular upper limit in the magnitude of the alternating magnetic field, if too large, the excitation coil 12 becomes large, preventing the device from being reduced in size. Thus, for example, if configured to be about that of the coil that generates an alternating magnetic field of a magnitude within a range corresponding to a region including two adjacent magnetic sections 101, an alternating magnetic field can be reliably applied to one magnetic section 101 and a part of a magnetic section 101 adjacent thereto; this is preferable. A more specific size of the excitation coil necessary to generate an alternating magnetic field of a magnitude within a range corresponding to a region including two adjacent magnetic sections 101 is preferably within a range of ⅔-2 times the length of one magnetic section 101 in the direction in which the magnetic sections are arranged. A description is provided with reference to FIG. 2(*c*). The size of the excitation coil 12 is preferably within a range of the length of the magnetic section 101 x1×⅔-x1×2. This is because, if the size of the excitation coil 12 is less than ⅔ of the length of one magnetic section 101, the magnitude of the magnetic field will be insufficient; if exceeding 2 times, the size of the device becomes large, which is not preferable.

The detection coil 13 should be a size that detects only the eddy current of the magnetic section 101 to be evaluated, of the eddy currents that are generated when the magnetic section 101 to be evaluated and the magnetic section 101 that is adjacent thereto are in a normal state. Specifically, the coil diameter of the detection coil 13 is configured to be a size that is equal to or less than the length of one magnetic section 101 to be evaluated in the direction in which the magnetic sections are arranged (the coil diameter of the detection coil 13 is configured to be equal to or less than the length x1 of the magnetic section 101 in FIG. 2C), as illustrated in FIG. 3. On the other hand, the width of the coil detection coil 13 is configured to be smaller than the magnetic section 101, as illustrated in FIG. 4.

The magnetic field that is generated by the eddy current generated in each magnetic section is generated so as to spread from the magnetic section; due to the effects of the shape of the magnetic section ends and the bonded portion of adjacent magnetic sections, an unevenness occurs in the magnetic field at the ends of the magnetic sections. Therefore, in order to measure the magnetic field that is generated by the eddy current that occurs in the magnets in a uniform state, the dimension of the detection coil 13 is preferably configured to be small with respect to the vertical and horizontal dimensions of the magnet. That is, the dimension M of the magnet is configured to be >the dimension DC of the detection coil 13.

Additionally, since the magnetic field that is generated by the eddy current that is generated in each magnetic section 101 is generated so as to spread from the magnetic section, the distance from the magnetic section 101 and the degree of misalignment from the center line c of the magnetic section 101, etc. also affect the measured value in the detection coil 13. Therefore, the distance between the detection coil 13 and the magnetic section 101 (gap G) is preferably sufficiently short. Also, during the measurement, by keeping the positional relationship between the detection coil 13 and the magnetic section 101 appropriate, such as by matching the center line C of the detection coil 13 and the center line c of the magnetic section 101 (C and c are in the same position in FIG. 4), the eddy current loss in the magnet can be evaluated with higher accuracy. This type of positional relationship between the center line C of the detection coil 13 and the center line c of the magnetic section 101 can be easily positioned with respect to both the evaluation magnet 51 and the master magnet 55 by using a holder 50.

The detection coil 13 is provided to the end surface of the divided portion of the C-shape of the yoke 11 so as to be coaxial with the excitation coil 12. Being coaxial means that the center of the coil diameter of the excitation coil 12 in the direction in which the magnetic sections 101 are arranged and the center of the coil diameter of the detection coil 13 in the direction in which the magnetic sections 101 are arranged are in the same position. By placing the detection coil 13 coaxially with the excitation coil 12, the eddy current generated in the magnetic section 101 can be reliably detected. However, for example, a mechanical placement error that is about the thickness of the coil wire is within the allowable range of being coaxial. In addition, upon actually making the device, the position of the detection coil 13 may be moved with respect to the position of the excitation coil 12 so as to be disposed in a position that is capable of detecting the eddy current most effectively.

A plurality of these detection coils 13 having different coil diameters (the size in the direction in which the magnetic sections 101 are adjacent) may be provided on the end surface of one yoke 11. Even if the sizes of the magnetic sections 101 of the evaluation magnet 51 change, immediately responding becomes possible by simply switching the detection coil 13 that is used to match the size of the magnetic section 101. In the case of providing a plurality of detection coils with different coil diameters in this manner, a switch should be attached between the plurality of detection coils, along with a voltmeter to switch the detection coil that is used in accordance with the size of the magnetic section of the evaluation magnet.

Figure 5A:
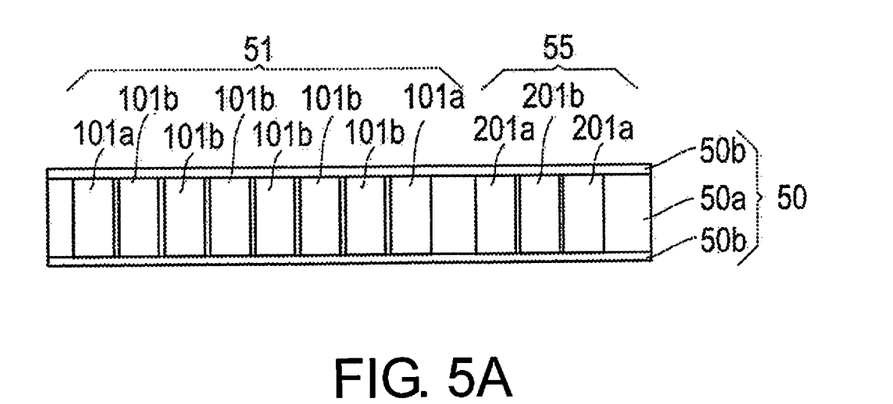
FIGS. 5A and 5B are schematic views showing the method of evaluating a magnet with the magnet evaluating device.
Figure 5B:
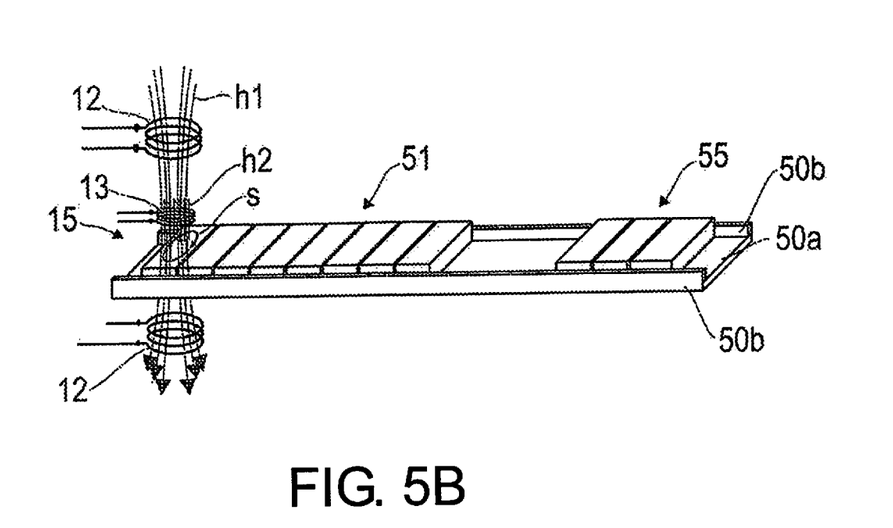
Figure 6:
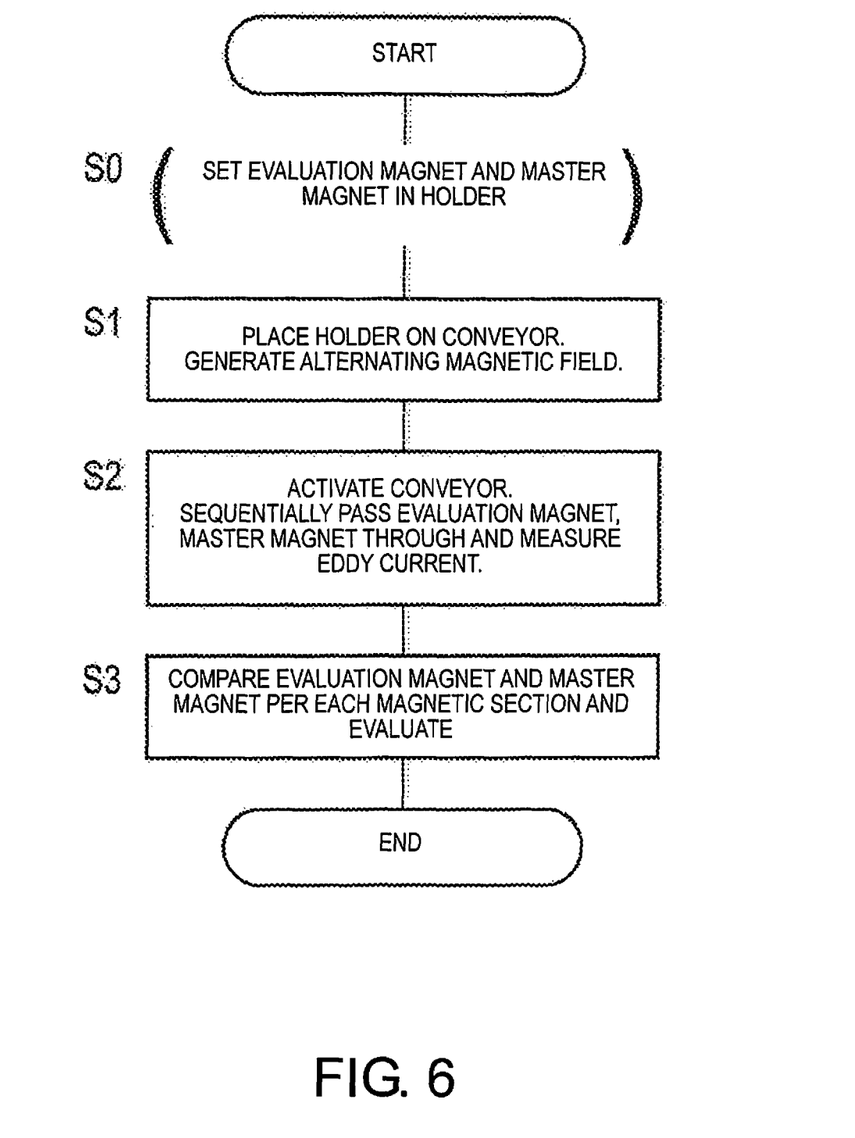
FIG. 6 is a flowchart illustrating the procedure of the evaluation method.

The method for evaluating a magnet that uses this magnet evaluating device 1 will be described next. FIGS. 5A and 5B are schematic views showing the method of evaluating a magnet using the magnet evaluating device 1. FIG. 6 is a flowchart illustrating the procedure of the evaluation method.

First, an overview of this evaluation method is described, with reference to FIGS. 5A and 5B. In this evaluation method, an evaluation magnet 51 to be evaluated and a master magnet 55, which is the subject of comparison, are passed through an evaluation position 15 of the magnet evaluating device consisting of a yoke 11, an excitation coil 12, and a detection coil 13. Then, the eddy current loss that is generated in the evaluation magnet 51 and the master magnet 55 is detected by the detection coil 13 and evaluated.

For the evaluation, first, the evaluation magnet 51 and the master magnet 55 are set with respect to the holder 50, as illustrated in FIG. 5A. Both the evaluation magnet 51 and the master magnet 55 are cleaved and reconnected magnets, as described above. In this FIG. 5A, the magnetic section at the end of the evaluation magnet 51 is referred to as an end magnetic section 101a. On the other hand, a magnetic section having magnetic sections on both adjacent sides is referred to as an intermediate magnetic section 101b. In the same way with the master magnet 55, the magnetic section at the end is referred to as the end magnetic section 201a, and a magnetic section having magnetic sections on both adjacent sides is referred to as an intermediate magnetic section 201b. The insulating material has been omitted from the drawing in FIG. 5A.

The holder 50 is formed so that the centers of the evaluation magnet 51 and the master magnet 55 in the width direction are aligned. The holder 50 in the drawing is provided with a bottom portion 50a for mounting the evaluation magnet 51 and the master magnet 55, as well as a wall member 50b that stands from both ends of this bottom portion 50a in the width direction and regulates the two end surfaces of the evaluation magnet 51 and the master magnet 55 in the width direction. The centers of both the evaluation magnet 51 and the master magnet 55 in the width direction are configured to be aligned by mounting the evaluation magnet 51 and the master magnet 55 in this holder 50.

At least one master magnet 55 may be set while setting one or more evaluation magnets 51 in one holder 50. However, when setting a plurality of evaluation magnets 51, two or more, in one holder 50, there is the risk that the time needed to measure the plurality of evaluation magnets 51 and the master magnet 55 increases, causing the ambient temperature and the like to change. Then, there is the risk that differences in the ambient temperature will affect the measurement results of the plurality of evaluation magnets 51 and the master magnet 55. Therefore, setting one evaluation magnet 51 and one master magnet 55 in one holder 50 is most preferable. By doing so, the time interval for measuring the evaluation magnet 51 and the master magnet 55 can be shortened, so that measurement is carried out in the same environment at all times. Of course, even if the measurement time increases, if the ambient temperature and the like do not change, at least one master magnet 55 and a plurality of evaluation magnets 51 may be set in one holder 50. During the evaluation, the evaluation magnet 51 and the master magnet 55, along with the holder 50, are sequentially passed through the evaluation position 15, where the yoke 11, the excitation coil 12, and the detection coil 13 are disposed, as illustrated in FIG. 5B. When the evaluation magnet 51 and the master magnet 55 pass through, an alternating magnetic field (a high-frequency magnetic field) h1 is thereby applied to the evaluation magnet 51 and the master magnet 55 by the excitation coil 12, and an eddy current s is generated in the evaluation magnet 51 and the master magnet 55. An induction current flows through the detection coil 13 due to the magnetic field h2 that is generated by the generated eddy current. Then, the evaluation of the eddy current loss is executed by observing the voltage (or the current) of the induction current generated in the detection coil 13.

By sequentially passing the evaluation magnet 51 and the master magnet 55 through the evaluation position 15 in this manner, the evaluation magnet 51 can be evaluated so that the ambient temperature and the external disturbance factors will be substantially the same environment and the same conditions.

The procedure of the evaluation method will be described next, with reference to FIG. 6.

Prior to evaluation, the evaluation magnet 51 and the master magnet 55 are set in the holder 50 (S0).

Then, the holder 50 is placed in a predetermined position of the conveyor 14, and an alternating magnetic field is generated by flowing a high-frequency wave through the excitation coil 12 (S1). Regarding the predetermined position for placing the holder 50 on the conveyor 14, the center of the evaluation magnet 51 and the master magnet 55 may be slightly offset from the center of the excitation coil 12 and the detection coil 13. This is because the present evaluation method only compares the evaluation magnet 51 and the master magnet 55; if the evaluation magnet 51 and the master magnet 55 are offset in the same way, the detected eddy current will also increase or decrease with the same tendency. If a part of the evaluation magnet 51 and the master magnet 55 is greatly offset so as to protrude from the excitation coil 12 and the detection coil 13, error is generated, which is not preferable. Therefore, as already explained, the dimension EC of the excitation coil 12 is configured to be >the dimension M of the magnet, and the dimension M of the magnet is configured to be >the dimension DC of the detection coil 13. Most preferably, the center of the widths of the evaluation magnet 51 and the master magnet 55 are placed to be at the center of the excitation coil 12 and the detection coil 13.

Next, the conveyor 14 is activated, and the evaluation magnet 51 and the master magnet 55 are sequentially passed through the alternating magnetic field, i.e., the evaluation position 15 to measure the eddy current (S1). The measurement of the eddy current is performed by measuring the induction current generated in the detection coil 13, while passing the evaluation magnet 51 and the master magnet 55, for each magnetic section 101 using a voltmeter 31. The value of the voltmeter 31 is input into the computer 32.

Next, the computer 32 determines the quality of the evaluation magnet 51 from the input value of the voltmeter 31 (S3). This determination is made by comparing the voltage of each magnetic section 101 of the master magnet 55 and the voltage of each magnetic section 101 of the evaluation magnet 51 (the determination method is described below).

Such a flow of evaluation can be controlled by, for example, a computer 32. First, the evaluation magnet 51 and the master magnet 55 that have been set in the holder 50 by an operator are placed on the conveyor 14. Then, the computer 32 activates the excitation coil 12 and the conveyor 14. The computer 32 then fetches the value of the induction current generated in the detection coil 13, which is measured by the voltmeter 31, for each magnetic section 101 and stores the values in a memory. The voltage values stored in the memory by the computer 32 are then compared and evaluated for each magnetic section of the evaluation magnet 51 and the master magnet 55. The voltage values stored in the memory may be configured to be stored as a file that can then be output later.

The starting and stopping, etc. of the excitation coil 12 and the conveyor 14 may be controlled by a line control device other than the computer 32, and the computer 32 may be configured to retrieve and evaluate the values of the voltmeter 31.

In the procedure described herein, the order for transfer into the magnetic field (evaluation position 15) was, first, the evaluation magnet 51, then, the master magnet 55; however, the master magnet 55 may be first, and the evaluation magnet 51 may be later. Even in that case, the evaluation can be done in the exact same way.

The evaluation principle and the evaluation method based thereon will be described next.

Figure 7:
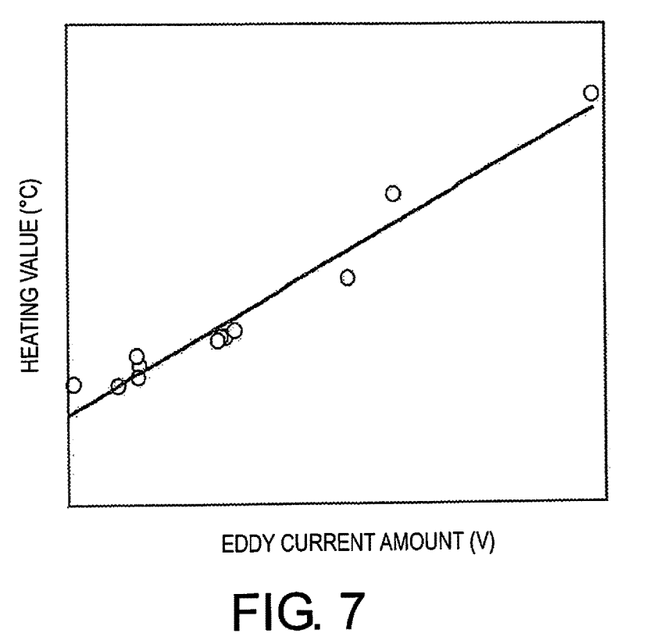
FIG. 7 is a graph illustrating the relationship between the eddy current amount and the heating value in the magnet.

FIG. 7 is a graph illustrating the relationship between the eddy current amount and the heating value in the magnet. In the drawing, the vertical axis is the heating value (° C.), and up indicates that the temperature is higher; the horizontal axis is the eddy current amount (V), and right indicates that the voltage is higher.

The heating value of the magnet was measured by putting a sample magnet in a vessel surrounded by heat insulating material, applying a magnetic field and measuring the temperature using a thermocouple attached to the magnet, as in the prior art (Japanese Laid-Open Patent Application No. 2003-234225). At this time, an eddy current is generated in the magnet by applying a magnetic field; when the temperature rises to a certain degree, the temperature reaches saturation and will no longer rise. Thus, the heating value was set to this saturation temperature.

On the other hand, the eddy current amount was measured by measuring the same magnet as the sample magnet used for measuring the heating value with a device similar to the present embodiment. The eddy current and the heating value generated in each of the sample magnets were configured to be different by preparing a plurality of sample magnets that were different sizes. All of the sample magnets were visually confirmed to be not defective (no cracks or defects).

There is a correlation between the detected voltage of the eddy current and the heating value, as illustrated in FIG. 7.

Figure 8:
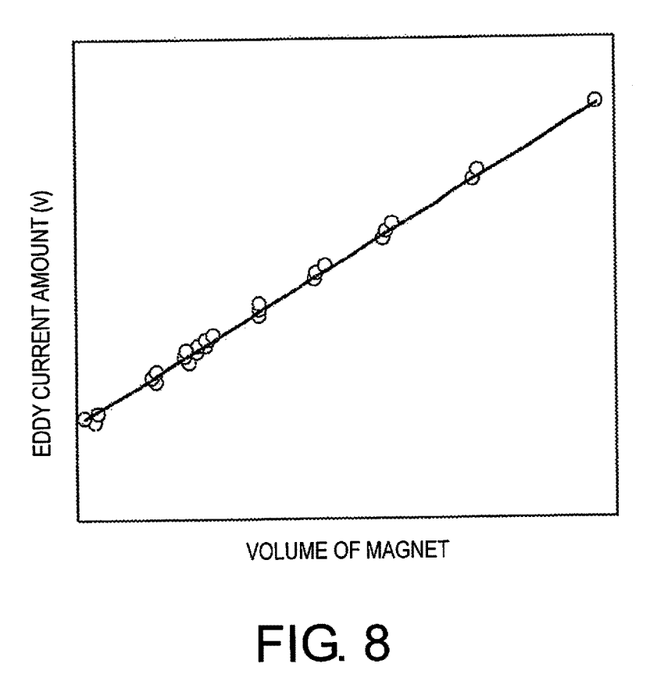
FIG. 8 is a graph illustrating the relationship between the eddy current amount in the magnet and volume of the magnet.

FIG. 8 is a graph illustrating the relationship between the eddy current amount in the magnet and volume of the magnet. In the drawing, the vertical axis is the eddy current amount (V), and up indicates that the voltage is higher; the horizontal axis is the size (volume) of the magnet, and right indicates that the volume is greater.

The results of FIG. 8 are measurements of the eddy current amount taken with a device similar to the present embodiment, using a plurality of sample magnets of different sizes, in the same way as in FIG. 7.

There is a correlation between the size of the magnet and the eddy current amount, as illustrated in FIG. 8.

These results of FIG. 7 and FIG. 8 show that the eddy current amount measured with the magnet evaluating device of the present embodiment correlates with the size of the measured magnet and the heating value that the magnet generates due to the eddy current. The eddy current loss can then be measured in the same way as with the insulated sample chamber of the prior art by using the magnet evaluating device of the present embodiment.

Figure 9:
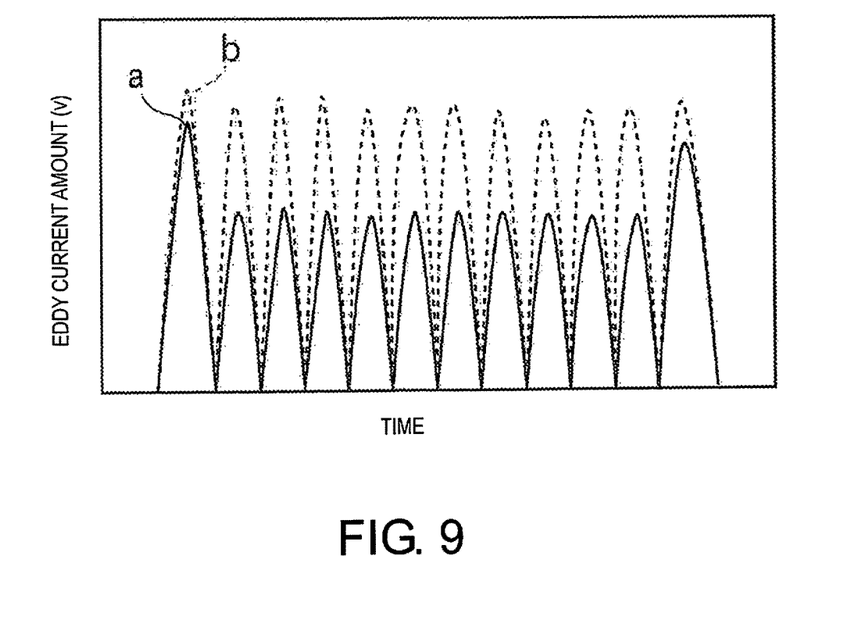
FIG. 9 is a graph illustrating the eddy current detection results in a cleaved and reconnected magnet and in a non-cleaved magnet.

Next, FIG. 9 is a graph illustrating the eddy current detection results in a cleaved and reconnected magnet and in a non-cleaved magnet. In the drawing, the vertical axis is the voltage (V) of the detection coil, and the horizontal axis is time (for moving the evaluation magnet in the direction in which the magnetic sections are arranged).

Also, a in the drawing is the measured value for the cleaved and reconnected magnet, which is the measured value for a cleaved and reconnected magnet made by connecting a plurality of magnetic sections with insulating material in between. b in the drawing is the measured value for the non-cleaved magnet, which is a measured value obtained by measuring each of the same magnetic sections as in the cleaved and reconnected magnet before the reconnection, separated to a degree that the eddy current of each will not affect another (that is, each magnetic section is measured separately). The measurement time intervals of the measured value b in the drawing are distanced for each magnetic section, since the gap between each magnetic section is actually separated; however, in the drawing, the voltage peak of the measured value b is adjusted to be illustrated in roughly the same position as the measured value a of the cleaved and reconnected magnet.

The drawing shows that the measured value a of the cleaved and reconnected magnet is less than the measured value b of the non-cleaved magnet. This is because, in the case of the cleaved and reconnected magnet, the measured value for each magnetic section is affected by the adjacent magnetic sections, causing the measured value to be smaller. In addition, a close look at this measured value a reveals that a magnetic section positioned at the end (the end magnetic section 101*a* in FIG. 5A) is higher than an intermediate magnetic section having magnetic sections on both adjacent sides (the intermediate magnetic section 101*b* in FIG. 5A).

Therefore, upon evaluation, the present embodiment is configured to compare a magnetic section at the end of the evaluation magnet with a magnetic section at the end of the master magnet, as well as to compare an intermediate magnetic section with magnetic sections on both adjacent sides with a magnetic section having magnetic sections on both adjacent sides in the master magnet. Referring to FIGS. 5A and 5B, the magnetic section 101*a* that is at the end of the evaluation magnet 51 is compared with the measured value for the magnetic section 201*a* at the end of the master magnet 55. On the other hand, the intermediate magnetic section 101*b* with magnetic sections on both adjacent sides is compared with the measured value for the magnetic section 201*b* with magnetic sections on both adjacent sides in the master magnet 55.

Upon comparing this type of evaluation magnet and master magnet, a threshold value may be set per each position of a magnetic section in the master magnet 55, and the measured value for magnetic sections in the evaluation magnet 51 in the same positional relationship may be compared.

Figure 10:
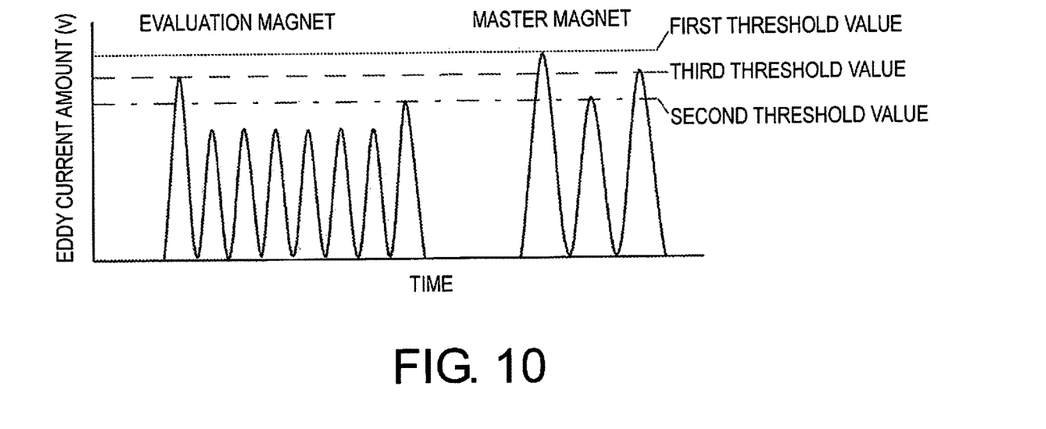
FIG. 10 is a graph illustrating the relationship between the evaluation magnet and a threshold value that is set for each position of the master magnet.

FIG. 10 is a graph illustrating the relationship between the evaluation magnet and a threshold value that is set for each position of the master magnet.

The measured value (voltage) of a magnetic section on the front end side of the traveling direction of the master magnet should be the first threshold value, the measured value (voltage) of an intermediate magnetic section should be the second threshold value, and the measured value (voltage) of a magnetic section on the rear end of the traveling direction should be the third threshold value. Then, upon evaluation, the measured values of the magnetic sections of the evaluation magnet in positions that correspond to the first to the third threshold values are compared with the first to the third threshold values.

The settings of the threshold values in FIG. 10 use the measured values (voltage) for the master magnet for each position as the threshold values; however, threshold values may be set with slight margins with respect to the measured values (voltage) for the master magnet. For example, when selecting as the master magnet, a magnet having an eddy current loss that is sufficiently small with respect to the required allowable range, values allowable as the eddy current loss and that are greater than the measured values are set as the threshold values. Specifically, when selecting as the master magnet, a magnet having an eddy current loss that is 10% or more less than the allowable range, voltage values that are about 10% greater than the measured values are set as the threshold values.

By setting the threshold values in this manner, an evaluation can be carried out, not with the measured values of the master magnet themselves, but with threshold values that are within the allowable range based on the measured values. For example, when using a magnet having better insulation properties due to the insulating material than the evaluation magnet upon selecting the master magnet, the eddy current loss of the master magnet will be higher than the desired value. In this case, if the quality is determined using the measured values of the master magnet themselves, a value that could withstand use, in terms of the eddy current loss of the evaluation magnet, could, nevertheless, be determined to be defective. Therefore, in this case, if the threshold values are set to be within a range allowable as the eddy current loss, based on the values measured for the master magnet, excessive defect determinations can be prevented.

Of course, the threshold values themselves may be the values measured for the master magnet. Even if configured in this way, evaluating the quality of the evaluation magnet can be carried out via a simple comparison with the threshold values, without having to read out values measured for the master magnet from the memory each time a comparison is made.

According to the embodiment described above, the following effects can be achieved.

(1) In the present embodiment, the excitation coil 12 generates an alternating magnetic field of a magnitude within a range corresponding to a region including an insulating material between at least one magnetic section 101 and another magnetic section 101 that is adjacent to the one magnetic section 101. On the other hand, that which has a coil diameter that is smaller than the length of one magnetic section 101 in the direction in which a plurality of magnetic sections 101 are arranged is used as the detection coil 13 for detecting an eddy current that is generated in the magnetic section 101 by the alternating magnetic field. Only the eddy current generated in one magnetic section 101 in a magnet (evaluation magnet 51 and the master magnet 55) made by connecting a plurality of magnetic sections 101 with an insulating material 103 in between can thereby be directly and reliably detected. Then, the evaluation magnet 51 and the master magnet 55 are continuously fed, the eddy currents thereof are measured, and the eddy currents measured for each magnetic section of the evaluation magnet 51 and the master magnet 55 are compared, so as to evaluate the evaluation magnet 51. The magnetic field that is generated by the eddy current generated in the magnet can thereby be measured at about the same time as acting on the alternating magnetic field, and evaluating and determining the quality of the evaluation magnet in an extremely short amount of time becomes possible.

Moreover, in the present embodiment, only the voltage value or the current value caused by the eddy current generated by the evaluation magnet 51 and the master magnet 55 are compared; therefore, converting the measured eddy current into a heating value that becomes the eddy current loss is not required; as a result, the evaluation of the magnet can be performed extremely simply. Additionally, by using the present embodiment, a conventional sample chamber covered with a heat insulating material is not required, which allows for a reduction in the size of the device. Accordingly, the device cost can be reduced.

Also, by making the detection coil 13 smaller than one magnetic section 101, even if a plurality of magnetic sections 101 are connected with insulating material 103 in between, the eddy current generated in each magnetic section 101 can be reliably detected. Accordingly, defects due to dielectric breakdown caused by defective insulating material in between the magnetic sections, as well as defects caused by defects and cracks (internal damage) present in each magnetic section 101, can be detected.

(2) The present embodiment is configured to compare the measured value of the voltage or the current generated in the detection coil 13 when an end magnetic section 101a, which is on the end of a plurality of magnetic sections 101 that configure the evaluation magnet 51, passes through a magnetic field, with a measured value of the voltage or the current that is generated in the detection coil 13 when an end magnetic section 201a, which is on the end of a plurality of magnetic sections that configure the master magnet 55, passes through a magnetic field. Additionally, the present embodiment is configured to compare the measured value of the voltage or the current generated in the detection coil 13 when an intermediate magnetic section 101b, which is one having magnetic sections on both adjacent sides, from among a plurality of magnetic sections 101 of the evaluation magnet 51, passes through a magnetic field, with a measured value of the voltage or the current generated in the detection coil 13 when an intermediate magnetic section 201b, which is one having magnetic sections on both adjacent sides, from among the plurality of magnetic sections of the master magnet 55, passes through a magnetic field.

When comparing the evaluation magnet 51 and the master magnet 55 in this manner, the quality of each magnetic section can be more accurately evaluated by comparing the measured values of magnetic sections in the same position.

(3) In the present embodiment, a first threshold value, a second threshold value, and a third threshold value were set corresponding to the positions of the magnetic sections that configure the master magnet 55. That is, a first threshold value based on the measured value of the voltage or the current generated in the detection coil 13 when, from among the plurality of magnetic sections of the master magnet 55, the end magnetic section 201a that is at the front end in the direction of transfer by the conveyor 14 (transfer unit) passes through a magnetic field; a second threshold value, based on the measured value of the voltage or the current generated in the detection coil 13 when, from among the plurality of magnetic sections of the master magnet 55, an intermediate magnetic section 201b having magnetic sections on both adjacent sides passes through a magnetic field; and a third threshold value, based on the measured value of the voltage or the current generated in the detection coil 13 when, from among the plurality of magnetic sections of the master magnet 55, the end magnetic section 201a that is at the rear end in the direction of transfer by the conveyor 14 (transfer unit) passes through a magnetic field.

Then, the measured value of the voltage or the current generated in the detection coil 13 when each magnetic section of the evaluation magnet 51 passes through the magnetic field is compared with one of the first to the third threshold values that corresponds to the position of each magnetic section.

In this manner, by setting threshold values that correspond to the positions of the magnetic sections that configure the master magnet 55, the values for the master magnet 55 can be measured, and the values that are within a predetermined allowable range from the measured values of the master magnet 55 can be set as the threshold values.

(4) The present embodiment is configured to prepare a holder for aligning the positions of the evaluation magnet 51 and the master magnet 55 and performing transfer after setting the evaluation magnet 51 and the master magnet 55 in this holder. Accordingly, positioning the evaluation magnet 51 and the master magnet 55 upon transferring becomes easy.

An embodiment according to the present invention was described above, but the present invention is not limited by the embodiment. For example, in the embodiment described above, the number of magnetic sections in both the evaluation magnet and the master magnet was set to three or more, but an evaluation magnet configured from two magnetic sections can also be evaluated. When evaluating an evaluation magnet configured from two magnetic sections, the master magnet to be used is preferably also configured from two magnetic sections. However, evaluation is also possible using a master magnet configured from three magnetic sections by comparing the measured value of an end magnetic section of this master magnet and the measured value of each of the two magnetic sections of the evaluation magnet. As already described, the measured value of each magnetic section is different when there is a magnetic section only on one adjacent side, as compared to when there are magnetic sections on both adjacent sides. Accordingly, even when using a master magnet with three magnetic sections, the measured value of the end magnetic section will be morphologically the same as a magnet consisting of two magnetic sections; therefore, by using the measured value thereof, evaluating an evaluation magnet configured from two magnetic sections becomes possible.

In addition to the above, various modifications to the present invention based on the configurations described in the Claims are possible, and they also belong within the scope of the present invention.

The invention claimed is:

1. A magnet evaluating device, comprising:
   an excitation coil configured to generate a magnetic field;
   a detection coil configured to detect an eddy current occurring in an evaluation magnet and a master magnet;
   a holder having the evaluation magnet and the master magnet set therein, the evaluation magnet being formed by connecting a plurality of evaluation magnetic sections with insulating material therebetween, and the master magnet being formed by connecting a plurality of master magnetic sections with insulating material therebetween;
   a transfer unit configured to transfer the evaluation magnet and the master magnet set in the holder through the magnetic field; and
   an evaluation unit configured to compare a first measurement and a second measurement, the first measurement measuring a first voltage or a first current generated in the detection coil when the evaluation magnet passes through the magnetic field, and the second measurement measuring a second voltage or a second current generated in the detection coil when the master magnet passes through the magnetic field.

2. The magnet evaluating device according to claim 1, wherein
   the plurality of evaluation magnetic sections comprises at least three evaluation magnetic sections and the plurality of master magnetic sections comprises at least three master magnetic sections,
   the evaluation unit is configured to compare the first measurement of the first voltage or the first current generated in the detection coil when an end evaluation magnetic section on an end of the plurality of evaluation magnetic sections of the evaluation magnet passes through the magnetic field, with the second measurement of the second voltage or the second current generated in the detection coil when an end master magnetic section on an end of the plurality of master magnetic sections of the master magnet passes through the magnetic field, and
   comparing the first measurement of the first voltage or the first current generated in the detection coil when an intermediate evaluation magnetic section having evaluation magnetic sections on both adjacent sides, from among the plurality of evaluation magnetic sections of the evaluation magnet, passes through the magnetic field, with the second measurement of the second voltage or the second current generated in the detection coil when an intermediate master magnetic section having master magnetic sections on both adjacent sides, from among the plurality of master magnetic sections of the master magnet, passes through the magnetic field.

3. The magnet evaluating device according to claim 2, wherein
   the evaluation unit,
   is configured to set a first threshold value, based on the second measurement of the second voltage or the second current generated in the detection coil when, from among the plurality of master magnetic sections of the master magnet, the end master magnetic section at a front end in a direction of transfer by the transfer unit passes through the magnetic field,
   a second threshold value, based on the second measurement of the second voltage or the second current generated in the detection coil when, from among the plurality of master magnetic sections of the master magnet, the intermediate master magnetic section having magnetic sections on both the adjacent sides passes through the magnetic field, and
   a third threshold value, based on the second measurement of the second voltage or the second current that is generated in the detection coil when, from among the plurality of master magnetic sections of the master magnet, the end master magnetic section at a rear end in the direction of transfer by the transfer unit passes through the magnetic field, and
   compares the first measurement of the first voltage or the first current generated in the detection coil when, from among the plurality of evaluation magnetic sections of the evaluation magnet, the end evaluation magnetic section at the front end in the direction of transfer by the transfer unit passes through the magnetic field with the first threshold value,
   compares the first measurement of the first voltage or the first current generated in the detection coil when, from among the plurality of evaluation magnetic sections of the evaluation magnet, the intermediate evaluation magnetic section having evaluation magnetic sections on both the adjacent sides passes through the magnetic field with the second threshold value, and compares the first measurement of the first voltage or the first current generated in the detection coil when, from among the plurality of evaluation magnetic sections of the evaluation magnet, the end evaluation magnetic section at the rear end in the direction of transfer by the transfer unit passes through the magnetic field with the third threshold value.

4. The magnet evaluating device according to claim 3, wherein the transfer unit is configured to transfer the evaluation magnet and the master magnet such that a first center of the evaluation magnet and a second center of the master magnet are aligned in a width direction of the evaluation magnet and the master magnet.

5. The magnet evaluating device according to claim 2, wherein the transfer unit is configured to transfer the evaluation magnet and the master magnet such that a first center of the evaluation magnet and a second center of the master magnet are aligned in a width direction of the evaluation magnet and the master magnet.

6. The magnet evaluating device according to claim 1, wherein the transfer unit is configured to transfer the evaluation magnet and the master magnet such that a first center of the evaluation magnet and a second center of the master magnet are aligned in a width direction of the evaluation magnet and the master magnet.

7. A magnet evaluation method that uses a magnet evaluating device, comprising:

generating, with an excitation coil, a magnetic field;

detecting, with a detection coil, an eddy current occurring in an evaluation magnet and a master magnet;

setting the evaluation magnet and the master magnet in a holder, the evaluation magnet being formed by connecting a plurality of evaluation magnetic sections with insulating material therebetween, and the master magnet being formed by connecting a plurality of master magnetic sections with insulating material therebetween;

transferring, with a transfer unit, the evaluation magnet and the master magnet set in the holder through the magnetic field; and evaluating the evaluation magnet by comparing a first voltage or a first current generated in the detection coil when the evaluation magnet passes through the magnetic field, with a second voltage or a second current generated in the detection coil when the master magnet passes through the magnetic field.

8. The magnet evaluating method according to claim 7, further comprising comparing a first measurement with a second measurement, the first measurement being the first voltage or the first current generated in the detection coil when an end evaluation magnetic section on an end of the plurality of evaluation magnetic sections of the evaluation magnet, passes through the magnetic field, and the second measurement being the second voltage or the second current generated in the detection coil when an end master magnetic section on an end of the plurality of master magnetic sections of the master magnet, passes through a magnetic field, and comparing the first measurement of the first voltage or the first current generated in the detection coil when an intermediate evaluation magnetic section having evaluation magnetic sections on both adjacent sides, from among the plurality of evaluation magnetic sections of the evaluation magnet, passes through the magnetic field, with the second measurement of the second voltage or the second current generated in the detection coil when an intermediate master magnetic section having master magnetic sections on both adjacent sides, from among the plurality of master magnetic sections of the master magnet, passes through the magnetic field, the plurality of evaluation magnetic sections comprising at least three evaluation magnetic sections and the plurality of master magnetic sections comprising at least three master magnetic sections.

9. The magnet evaluating device according to claim 8, further comprising setting a first threshold value, based on the second measurement of the second voltage or the second current generated in the detection coil when, from among the plurality of master magnetic sections of the master magnet, the end master magnetic section at a front end in a direction of transfer by the transfer unit passes through the magnetic field;

setting a second threshold value, based on the second measurement of the second voltage or the second current generated in the detection coil when, from among the plurality of master magnetic sections of the master magnet, the intermediate master magnetic section having master magnetic sections on both the adjacent sides passes through the magnetic field, and setting a third threshold value, based on the second measurement of the second voltage or the second current generated in the detection coil when, from among the plurality of master magnetic sections of the master magnet, the end master magnetic section at a rear end in the direction of transfer by the transfer unit passes through the magnetic field, and comparing the first measurement of the first voltage or the first current generated in the detection coil when, from among the plurality of evaluation magnetic sections of the evaluation magnet, the end evaluation magnetic section at the front end in the direction of transfer by the transfer unit passes through the magnetic field with the first threshold value, comparing the first measurement of the first voltage or the first current generated in the detection coil when, from among the plurality of evaluation magnetic sections of the evaluation magnet, the intermediate evaluation magnetic section having evaluation magnetic sections on both the adjacent sides passes through the magnetic field with the second threshold value, and comparing the first measurement of the first voltage or the first current generated in the detection coil when, from among the plurality of evaluation magnetic sections of the evaluation magnet, the end evaluation magnetic section at the rear end in the direction of transfer by the transfer unit passes through the magnetic field with the third threshold value.

* * * * *